United States Patent [19]

Wilson et al.

[11] Patent Number: 4,746,744

[45] Date of Patent: May 24, 1988

[54] METHOD OF PREPARATION OF 3,5-DICHLORO-2,4,6-TRIFLUOROPYRIDINE

[75] Inventors: Charles A. Wilson, Pittsburg; Alexander P. Fung, Martinez, both of Calif.

[73] Assignee: The Dow Chemical Company, Midland, Mich.

[21] Appl. No.: 921,563

[22] Filed: Oct. 22, 1986

[51] Int. Cl.$^4$ ............................................ C07D 213/61
[52] U.S. Cl. ..................................................... 546/345
[58] Field of Search ........................................ 546/345

[56] References Cited

U.S. PATENT DOCUMENTS 3,303,197  2/1967  Haszeldine et al. ............... 546/345

FOREIGN PATENT DOCUMENTS 1256082  12/1971  United Kingdom ............... 546/345
1306517  2/1973  United Kingdom ............... 546/345
1340421  12/1973  United Kingdom ............... 546/345

OTHER PUBLICATIONS

Finger, et al., J. Org. Chem., 28, 1666-1668.
Chambers, et al., J. Chem. Soc., 3573-6, 1964.
Banks, et al., J. Chem. Soc., 594-7, 1965.
Banks, et al., Chemisty & Industy, 835, 1964.
Chambers, et al., Proc. Chem. Soc., 83, 1964.

Primary Examiner—John M. Ford
Assistant Examiner—Robert C. Whittenbaugh

[57] ABSTRACT

The preparation of 3,5-dichloro-2,4,6-trifluoropyridine from pentachloropyridine and potassium fluoride was found to proceed in high yield and at a rapid rate with little tar formation when the reaction is conducted under essentially anhydrous conditions in N-methylpyrrolidone solvent at temperatures below 170° C. High yields of this intermediate for herbicides are obtained.

9 Claims, No Drawings

METHOD OF PREPARATION OF 3,5-DICHLORO-2,4,6-TRIFLUOROPYRIDINE

BACKGROUND OF THE INVENTION

The present invention relates to the preparation of 3,5-dichloro-2,4,6-trifluoropyridine from pentachloropyridine by halogen exchange.

The preparation of 3,5-dichloro-2,4,6-trifluoropyridine by processes involving the reaction of pentachloropyridine and potassium fluoride at temperatures of about 200° C. and higher is known. Dipolar, aprotic solvents have been utilized in these processes (U.S. Pat. No. 3,303,107). The process has also been taught to proceed satisfactorily at temperatures as low as 160° C. in a dipolar, aprotic solvent if an initiator such as ethylene glycol (British Pat. No. 1,306,517) or about 0.2 to about 2 percent water (British Pat. No. 1,256,082) is added. These processes all suffer because they provide only moderately high yields of the desired product, usually mixed with tarry degradation products, and generally require an excess of potassium fluoride to be employed for good results.

Improved processes for the production of 3,5-dichloro-2,4,6-trifluoropyridine are desirable as this compound is employed as an intermediate for the production of herbicides, such as 4-hydroxy-3,5-dichloro-2,6-difluoropyridine and 4-amino-3,5-dichloro-6-fluoro-2-pyridinyloxyacetic acid, and is useful among other things for fixing dyes to fabric.

SUMMARY OF THE INVENTION

It has now been found that 3,5-dichloro-2,4,6-trifluoropyridine is produced in high yield with very little tar formation when pentachloropyridine is contacted with potassium fluoride in N-methylpyrrolidone as solvent at about 100° C. to about 170° C. in the substantial absence of water and initiators. Vigorous agitation is usually employed. Under these conditions, little or no excess of potassium fluoride is required, the reaction proceeds at a rapid rate, and no detectable 2,3,4,6-tetrafluoro-5chloropyridine over-fluorination by-product is produced.

It is often advantageous to conduct the process in such a way that pentachloropyridine is continuously added to and 3,5-dichloro-2,4,6-trifluoropyridine is continuously removed by distillation from a slurry of potassium fluoride in N-methylpyrrolidone maintained at the reaction conditions of the invention.

DETAILED DESCRIPTION OF THE INVENTION

The improved process of present invention can be conducted in conventional equipment using conventional techniques known to those in the art so long as pentachloropyridine and potassium fluoride are contacted at about 100° C. to about 170° C. in N-methylpyrrolidone under essentially anhydrous conditions. Either batch or continuous reactors can be employed. It is preferred to employ a reactor equipped with means for removal of the 3,5-dichloro-2,4,6-trifluoropyridine by distillation as it forms. Means for the continuous addition of pentachloropyridine is also preferred. Systems having means for agitation in the reactor and which are suited for operation under sub- and/or super-atmospheric pressure are further preferred.

The product 3,5-dichloro-2,4,6-trifluoropyridine can be recovered from the reaction mixture obtained by conventional means. It is preferred to recover this product by distillation at atmospheric or sub-atmospheric pressure since its boiling point is appreciably below that of N-methylpyrrolidone, pentachloropyridine, and all intermediates formed. In some operations, it is most preferred to recover the product by distillation from the reaction mixture continuously as it forms during the process, while in other operations it is most preferred to recover it by distillation at the conclusion of the process. The recovered 3,5-dichloro-2, 4,6-trifluoropyridine can be additionally purified, if desired, by conventional means, notably by further distillation.

The order of addition of the pentachloropyridine, potassium fluoride, and N-methylpyrrolidone to the reaction vessel is not critical. It is however, preferred to prepare a slurry of potassium fluoride in N-methylpyrrolidone and subsequently add the pentachloropyridine. The pentachloropyridine can be added quickly or over an extended period of time either before or after the slurry of potassium fluoride in N-methylpyrrolidone is brought to the reaction temperature. In one preferred variation of the process, the pentachloropyridine is added continuously to the reactor and, at the same time and at approximately the same rate, the product 3,5-dichloro-2,4,6-trifluoropyridine is continuously removed by distillation.

The reaction consumes three moles of potassium fluoride for every mole of pentachloropyridine employed. While some of the desired product is formed regardless of the molar ratio of these reactants, it is generally preferred to employ about three moles of potassium fluoride per mole of pentachloropyridine. Deviations from this ratio are sometimes preferred, especially when a process involving the recycle of one or more starting materials or intermediates is employed. Mole ratios of about 2.6 to 1 to about 6 to 1 are common while those of about 2.85 to 1 to about 3.15 to 1 are especially advantageous. It is an important feature of the improved process of this invention that good yields of the desired product are obtained when approximately three moles of potassium fluoride per mole of pentachloropyridine are used. When three moles or less are employed, the insoluble salt remaining at the end of the reaction is essentially pure potassium chloride, which can be separated and has value without further purification to remove fluorides, tars, or organic side products.

Sufficient N-methylpyrrolidone solvent is employed to create a mobile slurry of potassium fluoride, but not so much as to make the process uneconomical. It is preferred to employ about 3 to about 20 pounds of solvent for every pound of potassium fluoride employed and most preferred to employ about 5 to about 10 pounds. Since the reaction produces very little tar and side reaction products, the solvent can be recycled without purification other than removal of the insoluble salts. Typically, the insoluble salts are removed by filtration or centrifugation either before or after distillation to remove the 3,5-dichloro-2,4,6-trifluoropyridine product.

The reaction is best conducted in the substantial absence of water. It is preferred to have a water content in the reaction mixture of less than about 500 ppm (0.05 percent) and more preferred to have less than about 100 ppm (0.01 percent). Generally, the less water present, the less tar formed and the better the yield obtained; amounts over 1000 ppm (0.1 percent) are clearly deleterious. Consequently, the reagents employed must either be anhydrous or means to dry them must be employed. It is convenient to remove unwanted water from the system by distillation. In preferred procedures, a slurry of potassium fluoride in N-methylpyrrolidone is prepared and heated to remove any unwanted water by distillation before the addition of pentachloropyridine. This can be done at atmospheric or sub-atmospheric pressure. A water azeotroping agent, such as toluene, can be added to facilitate the water removal. The water content can be monitored by coulometric titration.

The reaction is further best conducted in the substantial absence of initiators. While small amounts of initiators, such as amounts below 1000 ppm, are inconsequential to the reaction, large amounts significantly reduce the yield and increase tar formation.

The process can be carried out at temperatures as low as about 100° C., below which the reaction is very slow, and up to about 170° C., above which the yields significantly decrease and tar formation becomes a significant problem. It is preferred to maintain a temperature above about 130° C. and further preferred to maintain a temperature below about 160° C. and it is most preferred to maintain a temperature in the range of about 140° C. to about 160° C.

The reaction, when carried out in a batch operation, requires about two to about twenty hours. It is an important feature of the invention that the rate of reaction is relatively rapid at the temperatures employed.

The reaction mixture is most often vigorously agitated to ensure good contact between the reagents and good temperature control.

The pressure in the reactor is not critical to the reaction and any reasonable pressure can be employed. However, when operating so as to recover the product 3,5-dichloro-2,4,6-trifluoropyridine from the reaction mixture as it forms by distillation, it is often advantageous to use sub-atmospheric pressure as a means of reducing the boiling point of the product to a temperature well below the reaction temperature employed, thereby facilitating the recovery. 3,5-Dichloro-2,4,6-trifluoropyridine has a boiling point of 156° C. at 760 mm Hg. Pressures of about 10 mm Hg to ambient are typical and pressures of about 100 to about 200 mm Hg are generally preferred. In circumstances where the product is not removed by distillation as it forms, it is often convenient to carry out the reaction at atmospheric pressure or under a positive (super-atmospheric) pressure of an inert gas, such as nitrogen or argon.

The reagents required for the process, pentachloropyridine, potassium fluoride, and N-methylpyrrolidone are readily obtainable in the art or in commerce. It is preferred to employ potassium fluoride that is finely divided.

The following examples are presented to illustrate the process and should not be construed as limiting the claims.

EXAMPLE 1

A 5 liter (1) glass flask equipped with a stirrer, thermocouples in a thermowell extending into the reaction zone and connected to a recorder and a temperature controller, an encompassing heating mantle, a vacuum jacketed 10-tray Oldershaw column having a magnetically controlled fraction splitter and a water-jacketed product receiver, and a vacuum line having a pressure regulator and a manometer was charged with 3700 ml (3804 g) of N-methylpyrrolidone (NMP) and 435 g (7.5 moles) of potassium fluoride. The apparatus was evacuated to 170 mm Hg and heated to 150° C. with stirring to enable the drying of the system to less than 500 ppm by removal of about 200 ml of NMP and water. The vacuum was released and 502 g (2.00 moles) of pentachloropyridine (PCP) was added. The reaction temperature rose to 160° C. and then cooled to 150° C. The controller was reset to control at 150° C. The reaction mixture was sampled after four hours and analysis by quantitative gas-liquid chromatography using standards showed 75 percent conversion to 3,5-dichloro-2,4,6-trifluoropyridine with about 24 percent trichlorodifluoropyridines and about 1 percent of a tetrachloromonofluoropyridine. No PCP starting material was detected. The reaction was complete in 5 hours. The vacuum was reestablished at 185 mm Hg and removal of the desired product, 3,5-dichloro-2, 4,6-trifluoropyridine, was started. The reflux to takeoff ratio was set at 5:1 and the overhead temperature was 112° C. and the bottom temperature was 156° C. The total overhead material collected was 374 g of 97.7 percent purity product which is equivalent to 365 g of product or 90.4 percent of the theoretical yield. Analysis of the residue showed about 9 g of additional product remained unrecovered in the NMP residue. The residue was cooled and filtered to remove the by-product potassium chloride salt and to recover the NMP solvent. This was suitable for use in subsequent reactions.

EXAMPLE 2

A 5 l flask equipped as in Example 1 was charged with 3000 ml of reactant solvent from Example 1 and 500 ml of fresh NMP was added to renew the solvent volume to slightly over 3500 ml. To this amber red solution, 400 g (6.8 moles) of dry potassium fluoride was added. The potassium fluoride was dried under reduced pressure at 180° C. and ground to a fine powder while still hot. The reactor was closed and heated under a vacuum of 70 mm Hg at 140° C. with stirring to distill off about 40 ml of NMP. No water could be detected (less than 60 ppm). The vacuum was released and 502 g (2 moles) of PCP were added. The temperature was controlled at 150° C. The conversion of PCP to product was 58.3% complete in the first hour. The vacuum was reestablished at 170 mm Hg and product distillation started. The reflux to takeoff ratio was 5:1. The overhead distillate recovered was 379 g, 295 g being 99.1 percent pure product and the remaining 84 g being 94.4 percent pure. The recovered yield of 3,5-dichloro-2, 4,6-trifluoropyridine was 371.8 g, which is 92.0 percent of theory. The remaining 7.2 g was a mixture of partially fluorinated intermediates and NMP solvent. The reactor was allowed to cool and the distillation residue was filtered to remove the by-product potassium chloride salt and to recover the NMP solvent.

EXAMPLE 3

The 5 l reactor used in Example 1 was charged with about 3,300 ml of NMP from Example 2 and 250 ml of fresh NMP. Vacuum was established at 170 mm Hg and the reactor was heated with vigorous stirring to 150° C. A small amount of NMP was removed by distillation and the overhead temperature reached 145° C. The vacuum was released and 420 g of dry 99 percent potassium fluoride (7.16 moles) were added. The vacuum was reestablished and 20 ml of NMP were distilled overhead to dry the system to less than 100 ppm water. The vacuum was again released and 586 g (2.33 moles) of PCP were added. Vacuum was reestablished and the reactor temperature stabilized at 150° C. (control set point). During the first hour of reaction, the overhead temperature dropped to 108° C. Product takeoff was started with a reflux to takeoff ratio of 20:1. In the first six hours, 370 g of 99.8 percent pure 3,5-dichloro-2,4,6-trifluoropyridine were recovered. The reflux takeoff ratio was then changed to 60:1 and distillation continued. The second overhead cut contained 94.5 g of distillate, 86 g of which was the desired product, 1.9 g was a trichloro-difluoropyridine, and 6.6 g was NMP. The total 3,5-dichloro-2,4,6-trifluoropyridine collected overhead was 455.3 g (2.25 moles), which is 96.5 percent of theory. Including the trichloro-difluoropyridine recovered, the total recovery of useful products based on pentachloropyridine was 97.0 percent.

EXAMPLE 4

A 5 l Monel flask equipped as described in Example 1 was charged with 3,800 g of NMP, evacuated to 170 mm Hg and heated to 150° C. (control set point). About 210 ml of NMP and water were distilled overhead to dry the system to less than 500 ppm water. The vacuum was released and 406 g (7.00 moles) of potassium fluoride and 600 g (2.39 moles) of PCP were added. A sample of the reaction mixture was taken about five minutes after the addition and analyzed by gas-liquid chromatography. The reaction mixture was sampled and analyzed every 30 minutes and from this data a reaction profile was constructed. The reaction was complete in six hours, at which time it was allowed to cool. The mixture obtained was filtered to remove the insoluble salts and was distilled in a one inch 30-tray vacuum jacketed Oldershaw column to recover 346 g of 3,5-dichloro-2, 4,6-trifluoropyridine and 17.7 g of a trichloro-difluoropyridine overhead. Another 79.0 g of the latter remained in the residue. The yield of desired product was 73.6 percent of theory based on potassium fluoride and the overall recovery of fluoro-chloropyridines was 90.0 percent.

EXAMPLE 5

A 12 l Monel four-necked flask fitted as described in Example 1 was charged with 8.5 l of NMP. The flask was evacuated to 170 mm Hg, heated to 150° C. and about 500 ml of NMP and water were distilled overhead to dry the system to less than 500 ppm water. The vacuum was released and 1,400 g (24.1 moles) potassium fluoride and 2,020 g (8.0 moles) of PCP were added. The reaction mixture was padded with a positive (super-atmospheric pressure) nitrogen atmosphere and heated with vigorous stirring to 150° C. for eight hours. It was then cooled to 60° C. and removed from the reactor. The total weight of the reaction mixture was 11,725 g. The insoluble potassium chloride salt weight was calculated to be 1,789 g and the reaction solution weight to be 9,936 g. Gas-liquid chromatographic analysis showed the reaction solution to contain 1,232 g (6.09 moles) of the desired product, 288 g (1.32 moles) of a trichloro-difluoropyridine, and 60.6 g (0.26 moles) of a tetrachloro-monofluoropyridine. The total moles of product and intermediates accounted for in the reaction mixture was 7.67 moles or 95.9% accountability. The yield of 3,5-dichloro-2,4,6-trifluoropyridine was 76.1 percent of theory based on PCP used and 94.9 percent taking the recovered, recyclable intermediates into account.

What is claimed is:

1. An improved process for the preparation of 3,5-dichloro-2,4,6-trifluoropyridine from the reaction of pentachloropyridine and potassium fluoride wherein the improvement comprises contacting the pentachloropyridine and potassium fluoride in N-methylpyrrolidone solvent at about 100° C. to about 170° C. in the substantial absence of water and initiators.

2. A process according to claim 1 wherein 3,5-dichloro-2,4,6-trifluoropyridine is removed from the reaction mixture by distillation as it forms during the process.

3. A process according to claim 2 wherein the pentachloropyridine is continuously added to and the 3,5-dichloro-2,4,6-trifluoropyridine is continuously removed by distillation from a slurry of potassium fluoride in N-methylpyrrolidone.

4. A process according to claim 1 wherein 3,5-dichloro-2,4,6-trifluoropyridine is recovered from the reaction mixture by distillation at the conclusion of the process.

5. A process according to claim 1 wherein the contact is made under sub-atmospheric pressure.

6. A process according to claim 1 wherein the contact is made at atmospheric pressure.

7. A process according to claim 1 wherein the contact temperature is about 140° C. to about 160° C.

8. A process according to claim 1 wherein the water content is less than about 500 parts per million.

9. A process according to claim 1 wherein the mole ratio of potassium fluoride to pentachloropyridine is about 2.85 to 1 to about 3.15 to 1.

* * * * *